(12) United States Patent
Slassi et al.

(10) Patent No.: US 6,329,390 B1
(45) Date of Patent: Dec. 11, 2001

(54) 5-BICYCLOINDOLE COMPOUNDS

(75) Inventors: Abdelmalik Slassi; Jalaj Arora; Ashok Tehim, all of Mississauga (CA)

(73) Assignee: NPS Allelix Corp., Mississauga (CA)

( * ) Notice: Subject to any disclaimer, the term of this patent is extended or adjusted under 35 U.S.C. 154(b) by 0 days.

(21) Appl. No.: 09/116,946

(22) Filed: Jul. 17, 1998

(51) Int. Cl.⁷ .......................... A61K 43/42; A61K 43/40; C07D 241/36; C07D 471/20

(52) U.S. Cl. .................... 514/308; 514/309; 514/317; 544/349; 544/353; 544/354; 546/20

(58) Field of Search .............................. 546/201; 544/349, 544/353, 354; 514/308, 309, 317

(56) References Cited

PUBLICATIONS

International Publication No. WO 98/23587, International Publication Date Jun. 4, 1998.

*Primary Examiner*—John Kight
*Assistant Examiner*—Raymond Covington
(74) *Attorney, Agent, or Firm*—Arent Fox Kintner Plotkin & Kahn PLLC

(57) ABSTRACT

Disclosed herein are compounds selective for a 5-HT$_{1D}$ receptor, the compounds having the general formula (I):

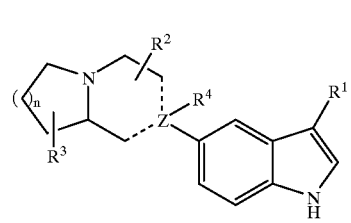

Also disclosed is the use of these compounds as pharmaceuticals to treat indications where stimulation of a 5-HT$_{1D}$ receptor is indicated such as migrane.

21 Claims, No Drawings

5-BICYCLOINDOLE COMPOUNDS

FIELD OF THE INVENTION

This invention relates to 5-bicycloindole compounds, to pharmaceutical compositions containing them and to their medical use, particularly in the treatment of CNS conditions.

BACKGROUND OF THE INVENTION

Through its interaction with receptors borne on neuronal and other cells, 5-hydroxytryptamine (5-HT or serotonin) exerts various physiological effects. Imbalances in this interaction are believed to be responsible for such conditions as anxiety, hallucination, migraine, chemotherapy-induced nausea and for disorders in sexual activity, car diovascular activity and thermoregulation, among others. From an improved understanding of the 5-HT receptor population, it is apparent that these effects are mediated selectively through individual types and subtypes of the 5-HT receptors. Migraine, for example, has been treated with ergolamine, dihydroergotamine, methylsergide and, most recently, sumatriptan, all of which presumably act at $5\text{-}HT_{1D}$ receptor subtype.

Current treatments for migraine, including sumatriptan, continue to have unwanted side effects. These include coronary vasospasm, hypertension and angina. Recent evidence suggests that sumatriptan's contraction of coronary arteries may be mediated by its stimulation of the $5\text{-}HT_{1B}$ (formerly $5\text{-}HT_{1D\beta}$) subtype of the 5-HT receptors (Kaumann, A. J. Circulation, 1994, 90:1141–1153).

Given the physiological and clinical significance of the $5\text{-}HT_{1D}$ receptor, and the potential side effect liability of stimulation of its $5\text{-}HT_{1B}$ receptor, it would be desirable to provide compounds that bin I with high affinity to the $5\text{-}HT_{1D}$ receptor. Such compounds would be medically useful for example to treat indications such as migraine and others for which administration of a $5\text{-}HT_{1D}$ ligand is indicated. Also they could be used diagnostically, for example to identify these receptors and to screen drug candidates.

SUMMARY OF THE INVENTION

According to one aspect of the invention, there are provided compounds of Formula I and a salt, solvate or hydrate thereof:

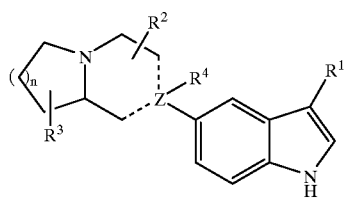

I wherein:

$R^1$ is selected from the group consisting of $CR^5R$ $CH_2NR^7R^8$ and a group of Formula II:

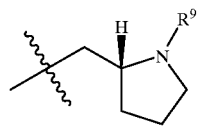

II $R^2$ is selected from the group consisting of H, OH, $C_{1-6}$alkyl and $C_{1-6}$alkoxy; $R^3$ is selected from the group consisting of H, OH, $C_{1-6}$alkyl, $C_{1-6}$alkoxy, $C_{1-6}$alkylthio and optionally substituted benzyloxy;
n is selected from the group consisting of an integer of from 1–3;
Z is selected from the group consisting of C and N;
——— represents a single or double bond provided at only one double bond is present in the ring at a time;
$R^4$ is selected from the group consisting of H. OH, $C_{1-6}$alkoxy or null, provided that when $R^4$ is selected from the group consisting of H, OH and $C_{1-6}$alkoxy, Z is C and ——— represents a single bond and when R 4 is null, either Z is C and ——— represents a double bond or Z is N and ——— represents a single bond; one of $R^5$ and $R^6$ is independently selected from H, $C_{1-6}$alkyl, $C_{1-6}$alkoxy and hydroxy and the other of $R^5$ and $R^6$ is H; $R^7$ and $R^8$ are independently selected from H and $C_{1-6}$alkyl or $R^7$ and $R^8$ form an alkylene bridge which optionally incorporates heteroatom selected from O, $NR^9$ and S, and which, together with the nitrogen atom to which they are attached, creates an optionally substituted 3- to 7-membered carbo- or heterocyclic ring; and
$R^9$ is selected from the group consisting of H, $C_{1-6}$alkyl and optionally substituted benzyl.

It is an aspect of the present invention to provide compounds that bind to the $5\text{-}HT_{1D}$ receptor.

It is another aspect of the present invention to provide compounds which bind selectively to the $5\text{-}HT_{1D}$ receptor, relative particularly to the $5\text{-}HT_{1B}$ receptor.

In another aspect of the present invention there are provided compositions containing the present compounds either for use as reagents, for example in the identification of $5\text{-}HT_{1D}$ receptor ligands or receptor ligands, or for pharmaceutical use to treat conditions where stimulation of the $5\text{-}HT_{1D}$ receptor is indicated.

It is another aspect of the present invention to provide a method effective to treat medical conditions for which stimulation of the $5\text{-}HT_{1D}$ receptor is indicated, such as to treat migraine.

These and other aspects of the present invention are described in greater detail hereinbelow.

DETAILED DESCRIPTION AND PREFERRED EMBODIMENTS

The term "loweralkyl" as used herein means straight and branched chain alkyl radicals containing from one to six carbon atoms and includes methyl, ethyl, propyl, isopropyl, t-butyl and the like.

The term "$C_{1-6}$alkoxy" as used herein means straight and branched chain alkoxy radicals containing from one to six carbon atoms and includes methoxy, ethoxy, propyloxy, isopropyloxy, t-butoxy and the like.

The term "optionally substituted benzyl" a used herein means an unsubstituted benzyl radical or benzyl radicals substituted on the phenyl ring with 1-3 substituents independently selected from halo, OH, $C_{1-6}$alkyl, $C_{1-6}$alkoxy, $C_{1-6}$alkylthio, $CF_3$ and $CF_3O$.

The term "optionally substituted benzyloxy" as used herein means an unsubstituted benzyloxy radical or benzyloxy radicals substituted on the phenyl ring with 1–3 substituents independently selected from halo, OH, $C_{1-6}$alkyl, $C_{1-6}$alkoxy, $C_{1-6}$alkylthio, $CF_3$ and $CF_3O$.

The term "alkylene bridge which optionally incorporates a heteroatom selected from O, $NR^9$ and S, and which, together with the nitrogen atom to which they are attached, creates an optionally substituted 3- to 7-membered carbo- or heterocyclic ring" as used herein means a 3- to 7-membered carbo- or heterocyclic radical which is optionally substituted with 1–2 substituents independently selected from halo, OH, $C_{1-6}$alkyl and $C_{1-6}$alkoxy and includes optionally substituted aziridinyl, azetidinyl, pyrrolidnyl, piperidinyl, morpholinyl and piperazinyl and the like.

The term halo as used herein means halogen and includes fluoro, chloro, bromo and the like, in both radioactive and non radioactive forms.

The term "pharmaceutically acceptable salt" means an acid addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyli , 2-phenoxybenzoic, p-toluenesulfonic acid and sulfonic acids such as methanesulfonic acid and 2-hydroxyethanesulfonic acid. Either the mono- or di -acid salts can be formed, and such salts can exist in either a hydrated, solvated or substantially anhydrous form. In general, the acid addition salt of these compounds are more soluble in water and various hydrophilic organic solvents, and generally demonstrate higher melting points in comparison to heir free base forms.

"Solvate" means a compound of Formula or the pharmaceutically acceptable salt of a compound of Formula I where n molecules of a suitable solvent are incorporated in a crystal lattice. A suitable solvent is physiologically tolerable at the dosage administered as the solvate. Examples of suitable solvents are ethanol, water and the like. When water is the solvent, the molecule is referred to as a hydrate.

The term "stereoisomers" is a general tern for all isomers of the individual molecules that differ only in the orientation of their atoms in space. It includes image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The present invention includes within it scope prodrugs of the compounds of Formula I. In general, such prodrugs will be functional derivatives of the compounds of Formula I which are readily convertible in vivo into the required compound of Formula I. Conventional procedures for the selection and preparation of suitable prodrug derivatives are described, for example, in "Design of Prodrugs" ed. H. Bundg Lard, Elsevier, 1985.

The compounds of the invention bind selectively (for example with 10-fold selectivity) to the to the serotonin 5-$HT_{1D}$ receptor, relative to the serotonin 5-$HT_{1B}$ receptor, as judged by in vitro binding affinities using, for example, the assay exemplified herein. Preferred compounds are those which bind with at least 25-fold selectivity to the 5-$HT_{1D}$ receptor, relative to the 5-$HT_{1B}$ receptor. More preferred compounds are those which bind with at least 50-fold selectivity to the 5-$HT_{1D}$ receptor, relative to the 5-$HT_{1B}$ receptor.

In embodiments of the invention, compounds of Formula I include those in which $R^1$ is selected from $CR^5R^6CH_2NR^7R^8$ and a group of Formula II:

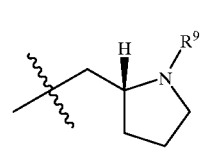

II

When $R^1$ is $CR^5R^6CH_2NR^7R^8$, one of $R^5$ and $R^6$ is independently selected from H, $C_{1-6}$alkyl, $C_{1-6}$alkoxy and hydroxy and the other of $R^5$ and $R^6$ is H, and $R^7$ and $R^8$ are independently selected from H and $C_{1-6}$alkyl or $R^7$ and $R^8$ form an alkylene bridge which optionally incorporates a heteroatom selected from 0, $NR^9$ and S, and which, together with the nitrogen atom to which they are attached, creates an optionally substituted 3- to 7-membered ring. Specifically, $R^5$ and $R^6$ are both H and R and $R^8$ are independently selected from H and methyl or $R^7$ and $R^8$ form an alkylene bridge which, together with the nitrogen atom to which they are attached, creates an unsubstituted 5- to 6-membered ring. More specifically, $R^5$ and $R^6$ are both H and $R^7$ and $R^8$ are either both Me or $R^7$ and $R^8$ form an alkylene bridge which, together with the nitrogen atom to which there are attached, creates an unsubstituted pyrrolidine ring. When $R^1$ is a group of Formula II, $R^9$ is selected from of H, $C_{1-6}$alkyl and benzyl, wherein benzyl is optionally substituted with 1–3 groups independently selected from halo, OH, $C_{1-6}$alkyl, $C_{1-6}$alkoxy, $C_{1-6}$alkylthio, $CF_3$ and $CF_3O$. Specifically, $R^9$ is selected from of H, methyl, ethyl and benzyl, wherein benzyl is optionally substituted with 1 group independently selected from halo, OH, methyl, methoxy, methylthio, $CF_3$and $CF_3O$. More specifically, $R^9$ is methyl., In further embodiments of the invention, R is selected from H, OH, $C_{1-6}$alkyl and $C_{1-6}$alkoxy, $R^3$is selected from H, OH, $C_{1-6}$alkyl, $C_{1-6}$alkoxy, $C_{1-6}$alkylthio and optionally substituted benzyloxy and $R^4$ is selected from null, H, OH and $C_{1-6}$alkoxy. Specifically, $R^2$ is selected from H and methyl, $R^3$ is selected from H, methyl and unsubstituted benzyloxy, and $R^4$ is selected from null, H and OH. More specifically, $R^2$ and $R^3$ are both H, and $R^4$ is independently selected from null, H and OH In other embodiments of the invention, n is selected from an integer of from 1 to 3, Z is either C or N, and ————— can be a single or double bond. In specific embodiments of the invention, n is selected from an integer of from 1–2, Z is either C or N, and ————— can be a single or double bond. In more specific embodiments of the invention, the bicyclic heterocycle at the 5-position of the indole ring is selected from octahydroindolizin-7-yl, 1,2,3,5,6,8a-hexahydroindolizin-7-yl and 1,2,3,5,8,8a-hexahydroindolizin-7-yl and the invention extends to cover all steroisomer thereof.

In embodiments of the invention, compounds of Formula I wherein R' is a group of Formula II, include those in which the stereochemistry of the 2-position of the pyrrolidine ring (in the group attached to the 3-position of the indole) is "R", that is, the pyrrolidine ring is derived from unnatural proline. The invention extends to cover all remaining structural and optical isomers of the various compounds of Formula I, as well as racemic mixtures thereof In embodiments of the invention, the compounds of Formula I include:
5-[(7-R,S)(8a-R,S)-7-Hydroxyoctahydroindolizin-7- Yl]-3-{[(2R)-N-methylpyrrolidin-2-yl]methyl}-1 H-indole;
5-[(7-R,S)(8a-R,S)-1 ,2,3,5,6,8a-Hexahydroindolizi -7-yI]-3-{[(2R)-N-methylpyrrolidin-2-yl]methyl}-1 H-indole;
5-[(7-R,S)(8a-R,S)-1,2,3,5,8,8a-Hexahydroindoliziri-7-yl]-3-{[(2R)-N-methylpyrrolidin-2-yl]methyl}-1 H-indole;
5-[(7-R,S)(8a-R,S)-Octahydroindolizin-7-yl]-3-{[(2R )-N-methylpyrrolidin-2-yl]methyl}-1 H-indole;
5-[(7-R,S)(8a-R)-7-Hydroxyoctahydroindolizin-7-yI] 3-[2-(N,N-dimethylamino)ethyl]indole;
5-[(7-R,S)(8a-S)-7-Hydroxyoctahydroindolizin-7-yl] 3-[2-(N,N-dimethylamino)ethyl]indole;
5-[(8a-R,S)-1,2,3,5,8,8a-Hexahydroindolizin-7-yl]-3 -[2-(N,N-dimethylamino)ethyl]indole;
5-[(8a-R,S)-1 ,2,3,5,6,8a-Hexahydroindolizin-7-yl]-3 -[2-(N,N-dimethylamino)ethyl]indole;
5-[(8a-R,S)-1 ,2,3,5,6,8a-Hexahydroindolizin-7-yl]- -(2-pyrrolidinylethyl)indole; and
5-[(8a-R,S)-1 ,2,3,5,8,8a-Hexahydroindolizin-7-yl]- -(2-pyrrolidinylethyl)indole.

In specific embodiments of the invention, the compounds of Formula I include:
5-[(7-R,S)(8a-R,S)-7-Hydroxyoctahydroindolizin-7- J]-3-{[(2R)-N-methylpyrrolidin-2-yl]methyl}-1 H-indole;
5-[(7-R,S)(8a-R,S)-1 ,2,3,5,6,8a-Hexahydroindolizin -7-yl]-3-{[(2R)-N-methylpyrrolidin-2-yl]methyl}-1 H-indole;
5-[(7-R,S)(8a-R,S)-1,2,3,5,8,8a-Hexahydroindolizir -7-yl]-3-{[(2R)-N-methylpyrrolidin-2-yl]methyl}-1 H-indole; and
5-[(7-R,S)(8a-R,S)-Octahydroindolizin-7-yI]-3-{[(2R )-N-methylpyrrolidin-2-yl]methyl}-1 H-indole.

In more specific embodiments of the invention, the compounds of Formula I include:
5-[(7-R,S)(8a-R,S)-7-Hydroxyoctahydroindolizin-7- 1]-3-{[(2R)-N-methylpyrrolidin-2-yl]methyl}-1H-indole; and
5-[(7-R,S)(8a-R,S)-1,2,3,5,8,8a-Hexahydroindolizii -7-yl]-3-{[(2R)-N-methylpyrrolidin-2-yl]methyl}-1 H-indole.

Acid addition salts of the compounds of formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. so sodium carbonate or potassium hydroxide, to liberate the free base which is then extracted into an appropriate solvent, such as ether. The free base is then separated from the aqueous portion, dried, and treated with the requisite acid to give the desired salt.

Also included within the scope of the invention are solvates of the invention. The formation of the solvate will vary depending on the compound and solvent used. In general, solvates are formed by dissolving the compound in the appropriate solvent and isolating the solvate by cooling or using an antisolvent. The solvate is typically dried or azeotroped under ambient conditions.

In accordance with other aspects of the invention, the compounds of the present invention can be prepared by processes analogous to those established in the art. Therefore, in general term, compounds of Formula Ia, wherein $R^1$–$R^3$ and n are as defined in Formula I, Z is C, $R^4$ is OH and ——— represents a single bond, can be prepared, for example, as shown below in Scheme 1. An indole reagent of Formula A, wherein $R^1$ is as defined in Formula I, Y is a suitable leaving group such a halo or triflate, (preferably bromo), and PG is a suitable protecting group, such a trialkylsilyl, arylsulfonyl and alkylsulfonyl group, preferably t-butyldimethylsilyl, can be treated with strong base, such as an alkyllithium, preferably t-butyllithium, followed by the addition of a ketone of, for example, Formula B, wherein $R^2$, $R^3$ and n are as defined in Formula I, to provide compounds of Formula D, wherein $R^2$, $R^3$ and n are as defined in Formula I and PG is as defined above. This reaction is performed in inert solvents, such as ether or tetrahydrofuran, at temperatures ranging from –100 to 0° C. Preferred conditions are tetrahydrofuran at –78 ° C. It should be noted that if two equivalents of a strong base are used in this reaction, it may not be necessary to protect the indole nitrogen. Removal of the protecting group on the indole nitrogen may be performed using standard procedures. For example, when PG is a trialkylsilyl group such as t-butyldimethylsilyl, compounds of Formula D are suitably deprotected using tetrabutylammonium fluoride in THF at room temperature, to provide compounds of Formula Ia, wherein $R^1$–$R^3$ and n are as defined in Formula I, $R^4$ is OH, Z is C and ——— is a single bond.

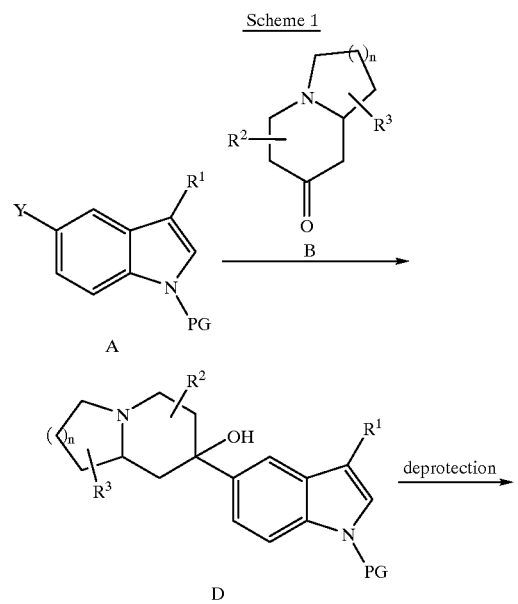

Scheme 1

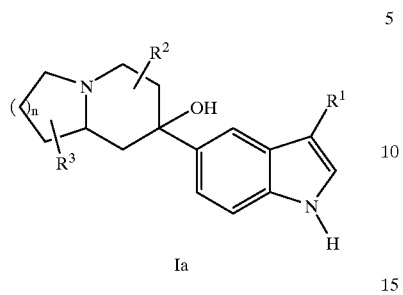

Ia

Compounds of Formula Ib and Ib', wherein $R^1$–$R^3$ and n are as defined in Formula I, Z is C, $R^4$ is null and ———— represents a double bond, may be prepared by coupling an indole of Formula E, wherein Y is a suitable leaving group such as halo or triflate (preferably bromo), X with a vinyl trialkylstannane of, for example, Formula F or G, wherein $R^2$, $R^3$ and n are as defined in Formula I, under standard metal catalyzed-cross coupling conditions as shown below in Scheme 2. It will be appreciated other metal coupling reagents could be used in place of the vinyl stanane, for example, a vinyl boronic acid, chloro zinc and the like. Suitable coupling conditions include refluxing the indole and heterobicyclic metal reagant in an inert solvent such as dimethylformamide or toluene in the presence of a palladium catalyst such as tetrakis(triphenylphosphine) palladium (0).

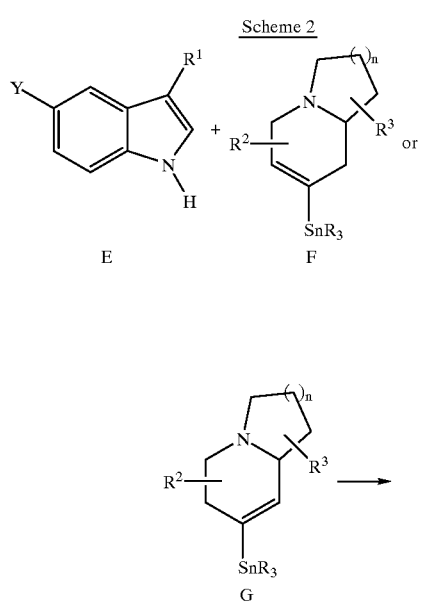

Scheme 2

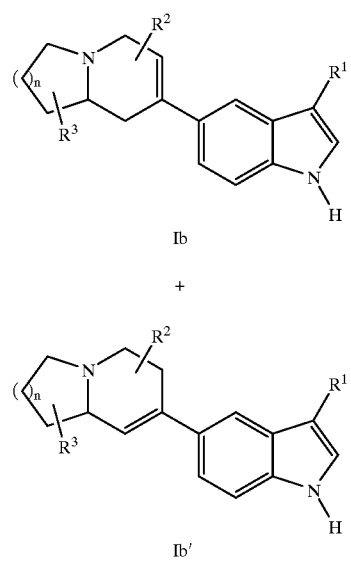

Ib

+

Ib'

Compounds of Formula I may be converted to other compounds of Formula I using standard conditions, for example dehydration of compounds wherein Z is C and $R^4$ is OH (Formula Ia), reduction or hydrogenation of compounds wherein Z is C and ———— represents a double bond (Formula Ib and Ib') or alkylation of compounds wherein any of $R^2$–$R^6$ is OH. Dehydration of compounds of Formula Ia wherein $R^4$ is OH can be performed, for example, by formation of the mesylate and elimination under basic conditions or in the presence of an acid such as trifluoroacetic acid in an inert solvent such as tetrahydrofuran, to provide compounds of Formula Ib and Ib' wherein Z is C, $R^4$ is null and ———— represents a double bond. This dehydration normally results in a mixture of both regioisomeric alkenes and is the preferred method for obtaining compounds of Formula Ib and Ib', wherein $R^1$–$R^3$ and n are as defined in Formula I, $R^4$ is null, Z is C and ———— represents a double bond. Reduction of the compounds of Formula Ib and Ib', wherein Z is C, $R^4$ is null and ———— represents a double bond, to provide compounds of Formula Ic wherein ———— is a single bond and $R^4$ is H, can be performed under standard hydrogenation conditions or using metahydride reducing agents. Suitable hydrogenation conditions are catalytic amounts of palladium on carbon in ethanol in a hydrogen atmosphere at room temperature. Suitable metal hydride reducing agents include lithium at minimum hydride or sodium cyanoborohydride. This reaction can be carried out in ether, tetrahydrofuran or ethanol/acid at temperatures ranging from 0 to 80° C. Alkylation of a hydroxy group of compounds of Formula I may be performed by treating such compounds of Formula I (for example where one of $R^2$–$R^4$ is OH) with a reagent of Formula R–Y, wherein Y is an appropriate leaving group, such as mesylate or halo, and R is $C_{1-6}$alkyl or benzyl, in the presence of a base in an inert solvent. Suitable conditions include potassium carbonate in acetonitrile or triethylamine in dichloromethane.

Compounds of Formula A may be prepared from compounds of Formula E using standard protecting group methodologies. For example, the t-butyldimethylsilyl protecting group may be attached to the indole nitrogen by treating a compound of Formula E, wherein $R^1$ and Y are as defined above, with a strong base, such as sodium and hydrogenation ($H_2$, Pd/C in methanol) when R is benzyl, and alkylated on he pyrrolidine nitrogen by treatment with $R^9$—Y, wherein $R^9$ is as defined in Formula I and Y is a suitable leaving group such as halogen, in the presence of a base in an inert solvent to provide intermediates L and M respectively. Suitable alkylation conditions include potassium carbonate in acetonitrite or triethylamine in dichloromethane. Temperatures can be in the range of 25 to 85° C., preferably at room temperature. Intermediate M can be reduced as described above to provide compounds of Formula E', wherein $R^9$ is as defined in Formula I.

Scheme 3

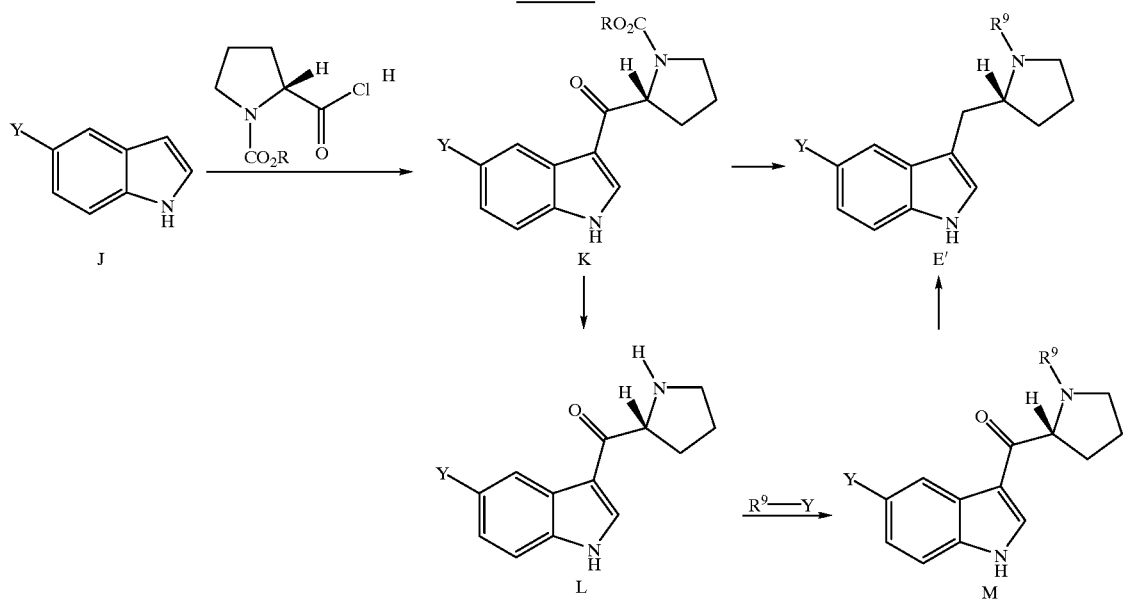

hexamethyldisilazide, in an inert solvent, such as tetrahydrofuran, at a temperature in the range of –40 to 30° C., suitably 25° C., followed by the addition of t-butyldimethylsilyl chloride at a reduced temperature, suitably 0° C.

Compounds of Formula E', wherein $R^1$ is a group of Formula II, wherein $R^9$ is as defined in Formula I, and Y is a suitable having group such as halo or triflate (preferably bromo), can be prepared a shown in Scheme 3. A compound of Formula H (derived from unnatural proline), in which R is, for example, benzyl or t-butyl, can be condensed with indole J, wherein Y is as defined above, typically by first converting the indole to a magnesium derivative by reaction with a suitable Grignard reagent, such as t-butyl- or ethylmagnesium bromide, in an inert solvent. Then the magnesium derivative so formed can be reacted in situ with reagent of Formula H to provide intermediates of Formula K. Suitable solvents include tetrahydrofuran and diethylether (which is preferred). The reaction can be conducted at temperatures ranging from –30 to 65° C., suitably at room temperature. Intermediate K may be reduced with hydride reducing agents directly to provide a compound of Formula E', wherein $R^9$ is methyl. The preferred reducing conditions are lithium aluminum hydride in tetrahydrofuran at a temperature of around 65° C. Alternatively, intermediate K can be deprotected under standard conditions, for example sodium hydroxide in methanol when R is other than benzyl Compounds of Formula E", wherein $R^1$ is $CR^5R^6CH_2NR^7R^8$, wherein $R^5$–$R^8$ are as defined in Formula I, and Y is a suitable leaving group such as halo or triflate (preferably bromo), can be prepared by reaction of indole J with oxalyl chloride followed by reaction with the appropriate amine to provide an intermediate of Formula N, wherein Y is as defined above and $R^7$ and $R^8$ are as defined in Formula I, as shown in Scheme 4. This reaction is normally conducted in an inert solvent such as diethyl ether (preferred) or dichloromethane, and at temperatures in the rang of 0–65° C., preferably 25–65° C. Intermediate N can be reduced to the desired compound of Formula E" using standard conditions, e.g. using lithium aluminum hydride, lithium borohydride or diborane as reducing agent, in an inert solvent such as tetrahydrofuran, dioxane or diethyl ether at temperatures of from about 25–100° C. Preferred is the reduction with lithium aluminum hydride in tetrahydrofuran at a temperature of about 65° C. If this reduction is carried out with a smaller amount of reducing agent, compounds of Formula E", wherein one of $R^5$ and $R^6$ is OH can be isolated. This hydroxy group can then be alkylated using standard conditions (for example $C_{1-6}$alkyl halide and potassium carbonate in acetonitrile) or displaced with, for example, $C_{1-6}$alkyl lithium reagents, to provide compounds of Formula E" wherein one of $R^5$ and $R^6$ is $C_{1-6}$alkoxy or $C_{1-6}$alkyl, respectively.

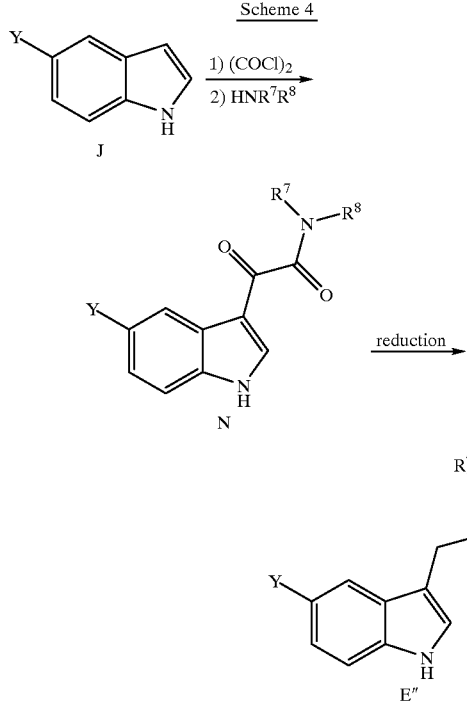

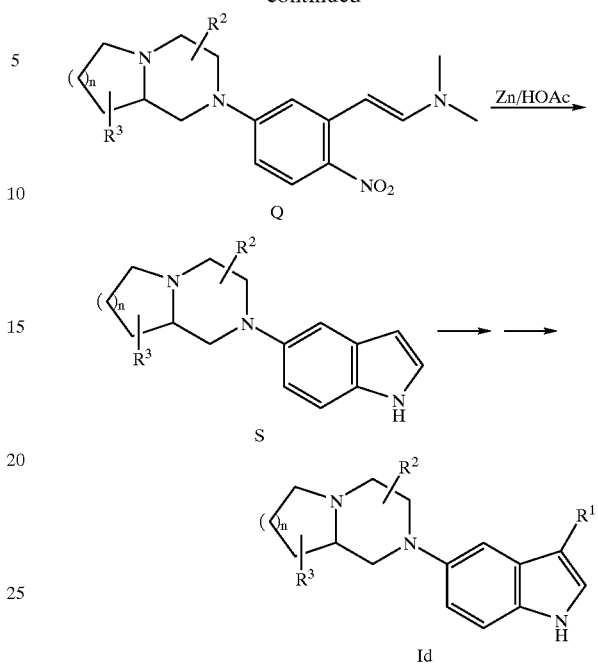

Compounds of Formula Id, wherein Z is N, may be prepared as shown in Scheme 5. A reagent of Formula O, wherein Y is a suitable leaving group, such as halo, preferably fluoro, is treated with a bicyclic piperazine of Formula P, wherein $R^2$, $R^3$ and n are as defined in Formula I, in the presence of N,N-dimethylformamide dimethyl acetal in an inert solvent, such as N,N-dimethylformamide, according to procedures described in *J. Org. Chem.* 51, 1986:5106–5110, to provide intermediates of Formula Q, wherein $R^1$, $R^2$ and n are as defined in Formula I. Cyclization to indole S, wherein $R^1$, $R^2$ and n are as defined in Formula I, may be achieved by treating intermediate Q with zinc in acetic acid as described in *J. Org. Chem.* 51, 1 86:5106–5110. Elaboration of compounds of Formula S to compounds of Formula Id can be performed using the sequences described above for the conversion of indole J into compounds of Formula E (see Schemes 3 and 4)

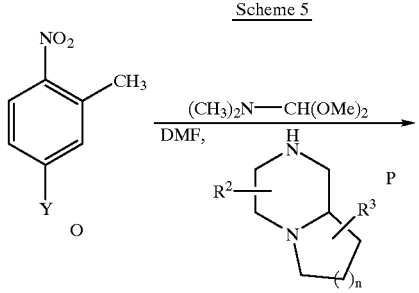

Compounds of Formula S may also be prepared by treating a compound of Formula J, wherein Y is an appropriate leaving group such as halo, preferably bromo, having a suitable protecting group on the indole nitrogen with an excess of a piperazine of Formula P wherein $R^2$, $R^3$ and n are as defined in Formula I, as described in Nishiyama, et al. Tetrahedron Lett. 39, 1998:617–620. Removal of the protecting group provides compounds of Formula S and elaboration of the indole 3-position as described above, provides compounds of Formula Id, wherein $R^1$–$R^3$ and n are as defined in Formula I.

The bicyclic piperidinones B and piperazin is P, wherein $R^2$, $R^3$ and n are as defined in Formula I, are either commercially available or can be prepared using procedures known in the art. For example, bicyclic piperidinones of Formula B may be prepared according to procedures described in King, F. D., J. Chem. Soc. Perkin Trans. I, 1986:447–453 and bicyclic piperazines of Formula P may be prepared according to procedures described in Power, P. et al., U.S. Pat. No. 5,576,314; Saleh, M. A. et al. J. Org. Chem. 58, 1993:690–695; Urban, F. J. Heterocyclic Chem 32, 1995:857–861; Bright, G. et al. WO 90/08148; de Costa, B. R. et aL J. M Ed. Chem. 36, 1993:2311–2320; and Botre, C. et al. J. Med. Chem. 29, 1986:1814–1820. The bicyclic piperidines F and G may be prepared from piperidinone B using standard chemistries, for example, by reacting the ketone with a base, such as lithium diisopropylamide or triethylamine, and a suitable agent, such as N-phenyltriflimide or triflic anhydride, and converting the resulting triflate to a compound of Formula F or G by treatment with, for example, a palladium catalyst and a bis(trialkyltin). Alternatively, bicyclic piperidines F and G may be prepared by forming the tosylhydrazone of a compound of Formula B and using standard Shapiro conditions, trap the vinyl a ion with a suitable reagent like tributyltin chloride.

The indoles of Formula J and 2-nitrotoluenes of Formula O are either commercially available or may be prepared using methods known in the art.

It should be noted that one skilled in the art would realize that the sequence of reactions described above for the preparation of compounds of Formula I can be varied. For example, when Z is the group at the indole 5-position may be incorporated into the molecule before the addition of the group at the indole 3-position.

In some cases, the chemistries outline above may have to be modified, for instance by use of protecting groups to prevent side reactions due to reactive groups, such as reactive group ,attached as substituents. This may be achieved be means of conventional protecting groups, as described in *Protective Groups in Organic Chemistry,* ed. McOmie, J.F.W. Plenum Press, 1973; and Greene, T. W. & Wuts, P.G.M., *Protective Groups in Organic Synthesis,* John Wiley & Sons, 1991.

In another embodiment of the invention, the present compounds can be used to distinguish $5\text{-HT}_{1D}$ receptors from other receptor subtypes, for example glutamate or opioid receptors, within a population of receptors, and in particular to distinguish between the $5\text{-HT}_1 1$ and other 5-HT receptor subtypes. The latter can be achieved by incubating preparations of the $5\text{-HT}_{10}$ receptor and one of the other 5-HT receptor subtypes (for example $5\text{-HT}_{1B}$) with a $5\text{-HT}_{1D}$-selective compound of the invention and then incubating the resulting preparation with a radiolabeled serotonin receptor ligand, for example [3H]-serotonin. The $5\text{-HT}_1\text{D}$ receptors are then distinguished by determining the difference in membrane-bound activity, with the $5\text{-HT}_{1D}$ receptor exhibiting lesser radioactivity, i.e., lesser [$^3$H]-serotonin binding, than the other 5-HT receptor subtype.

In an aspect of the invention, the compound is provided in labeled form, such as radiolabeled form, e. g. labeled by incorporation within its structure $^3$H or $^{14}$C or by conjugation to $^{125}$I. In another aspect of the invention, the compounds in labeled form can be used as competitive ligands to identify $5\text{-HT}_{1D}$ receptor ligands by techniques common in the art. This can be achieved by incubating the receptor or tissue i the presence of a ligand candidate and then incubating the resulting preparation with an equimolar amount of radiolabeled compound of the invention such as [3H]-5-[(7-R,S)(8a-R,S)-1 ,2,3,5,8,8a-Hexahydroindolizin-7-yl]-3-{[(2R -N-methylpyrrolidin-2-yl]methyl}-1 H-indole. $5\text{-HT}_{1D}$ receptor ligands are thus revealed as those that are not significantly displaced by the radiolabeled compound of the present invention. Alternatively, $5\text{-HT}_1\text{D}$ receptor ligand candidates may be identified by first incubating a radiolabeled form of a compound of the invention then incubating the resulting preparation in the presence of the candidate ligand. A more potent $5\text{-HT}_1\text{D}$ receptor ligand will, at equimolar concentration, displace the radiolabeled compound of the invention.

The present compounds are useful a pharmaceuticals for the treatment of various conditions in which the use of a $5\text{-HT}_{1D}$ ligand is indicated, such as for the treatment of migraine, cluster headache and portal tension, a condition characterized by increased portal vein blood flow and typically associated with cirrhosis of the liver.

For use in medicine, the compounds of the present invention can be administered in a standard pharmaceutical composition. The present invention therefore provides, in a further aspect, pharmaceutic compositions comprising a pharmaceutically acceptable carrier and at least o e compound of Formula I, or a pharmaceutically acceptable salt, solvate or hydrate thereof, in an amount effective to stimulate the $^5\text{-HT}_{1D}$ receptor.

The compounds of the present invention my be administered by any convenient route, for example by oral, parenteral, buccal, sublingual, nasal, rectal or transdermal administration and the pharmaceutical compositions will be formulated accordingly.

Compounds of Formula I and their stereoisomers, solvates, hydrates or pharmaceutically acceptable salts for oral administration can be formulated as liquids, for example syrups, suspensions, solution or emulsions, or as solid forms such as tablets, capsules and lozenges, or they may be presented as a dry product for constitution with water or other suitable vehicle before use. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent (e.g. sorbitol syrup, methyl cellulose or hydrogenated edible fats), preservative (e.g. methyl or propyl p-hydroxybenzoates or sorbic acid), flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

The compounds of the invention may be formulated for parenteral administration by injection, including using conventional catheterisation techniques or infusion. Formulations for injection may be presented in unit dosage form, e.g. in ampoules or in multi-dose containers, with an added preservative. Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil, and may contain formulatory agents such as suspending, stabilizing and/or dispersing agents. Alternatively, the solution can be lyophilized and then reconstituted with a suitable solvent just prior to administration.

Compositions for nasal administration may conveniently be formulated as aerosols, drops, gels and powders. Aerosol for formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage for forms can also take the form of a pump-atomizer. Capsules and cartridges of e.g. gelatin for use in an inhaler or atomizing device may be formulated containing a powder mix of a compound of the invention and a suitable powder base such a lactose or starch.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of for example suppositories or retention enemas, containing a conventional suppository base such as cocoa butter or other glycerides.

A proposed dose of the compounds of the invention for oral, buccal, sublingual or rectal administration to human (about 0 kg body weight) for the treatment of migraine is 0.1 mg to 500 mg, for example 0.5 mg to 100 mg, preferably 1 mg to 50 mg, of active ingredient per dose which could be administered up to 8 times per day, more usually 1 to 4 times per day. It will be appreciated that it may be necessary to make routine changes to the dosage depending on the age and weight of the patent as well as the severity of the condition to be treated. It should be understood that unless otherwise indicated, the dosages are referred to in terms of the weight of the compound of Formula I calculated as the free base.

The overall daily dosage administered by injection may be in the range of 0.01 mg to 100 mg, preferably between 0.1 mg to 50 mg, e.g., between 1 mg and 25 mg, of a compound of Formula I or a pharmaceutically acceptable salt, solvate or hydrate thereof calculated as the free base, the compound being administered 1 to 4 doses per day.

Aerosol formulations are preferably arranged so that each metered dose or "puff" delivered from a pressurized aerosol contains 0.1 to 10 mg of a compound of the invention, and each dose administered via capsules and cartridges in an inhaler contains 0.1 to 50 mg of a compound of the invention. Administration may be several times daily, for example 2 to 8 times, giving for example 1,2 or 3 doses each time. The overall daily dose by inhalation will be similar to that for oral administration.

The compounds of the invention may, if desired, be administered in combination with one or more other therapeutic agents, such as analgesics, anti-inflammatory agents and anti-nauseants.

Experimental Examples

Example 1(a): (R)-3-(N-Benzyloxycarbonylpyrrolidi i-2-ylcarbonyl)-5-bromo-1H-indole To a stirred solution of N-benzyloxycarbonyl-R-proline (2.5 g, 10.0 mmol) in anhydrous methylene chloride was added a solution of oxalyl chloride (2M solution in methylene chloride, 7 mL, 15.0 mmol). he resulting mixture was stirred at room temperature under argon for 2 hours. The solvent and excess oxalyl chloride were evaporated under reduced pressure and the crude product washed with hexane (3×10 mL) and evaporated to dryness to provide N-benzyloxycarbonyl-R-proline acid chloride which was used directly for the next reaction.

N-Benzyloxycarbonyl-R-proline acid chloride from the above reaction was dissolved in anhydrous diethyl ether (30 mL) and added at 0° C. to a solution of 5-bromoindole (2.9 g, 15.0 mmol) and t-butylmagnesium chloride (2M solution in diethyl ether, 8.3 mL, 16.5 mmol) in anhydrous diethyl ether (30 mL). The resulting mixture was stirred at room temperature under argon for 45 minutes and then ethyl acetate (150 mL) and saturated sodium bicarbonate (30 mL) were added. The organic lay was dried and evaporated under reduced pressure to provide a yellow oil. The title compound was crystallized using hexane/ethyl actate (9:1 ) to provide a white solid (3.07 g, 72%). mp 95–96° C. In a like manner, the following addition compound was prepared:

(b) (S)-3-(N-Benzyloxycarbonylpyrrolidin-2-ylcarbonyl)-5-bromo-I H-indole: from N-benzyloxycarbonyl-S-proline. mp 95–96° C.

Example 1 (a): 5-Bromo-3-(1-pyrrolidinylglyoxyl)-1 H indole

To a solution of 5-bromoindole (3.92 g, 20 mmol) in the (50 mL), cooled to 0° C., was added a solution of oxalyl chloride in dichloromethane (2M, 10 mL) dropwise. The resulting mixture was stirred at room temperature overnight and then cooled to 0° C. and pyrrolidine (6.7 mL, 80 nmol) was added dropwise. After stirring for 2 hours at room temperature, the mixture was poured into water (50 mL) and extracted with dichloromethane (3×100 mL). The combined organic phases were dried over sodium sulfate and evaporated to a white amorphous solid which was washed with ethyl acetate (50 mL) to give the title compound (2.87 g, 45%). m 212–213° C.; $^1$H NMR (CDCl$_{3, 300}$ MHz)δ: 10.69 (s,1 H), 8.49 (d, J =1.5 z,1 H), 7.87 (d, J =3.0 Hz, 1H), 7.31 (dd, J =8.6,1.5Hz, IH), 7.17 (d,J=6Hz, 1H), 3.59 (m, 4H), 1.94 (m,4H).

In a like manner, the following additional compound was prepared:

(b) 5-Bromo-3-(N,N-dimethylaminoglyoxyl)-1 H-indole, from dimethylamine; $^1$H NMR (CDCl$_3$, 300 MHz)δ: 10.05 (s,1 H), 8.48 (d, J 1.5 Hz, 1 H), 7.71 (d, J =2.4 Hz, 1H), 7.35 (dd, J=1.5, 8.5 Hz, 1H), 7.19 (d, J =8.5 Hz, 1H), 3.10 (s, 3H), 3.06 (s, 3H).

Example 3(a): 5-Bromo-3-[2-(N,N-dimethylamino)ethyl]-1 H-indole

A solution of LAH (39 mL, 1 M in THF, 39 mmol) was added slowly to a cooled (0° C.) solution of 5-bromo-3-(N, N-dimethylaminoglyoxyl)-1 H-indole (Example 2b, 2.82 g, 9.5 mmol) in THF (100 mL). Once the addition was completed, the reaction mixture was stirred at reflux overnight prior to quenching with sodium sulfate decahydrate. The product was taken into ethyl acetate, filtered to remove the solid residue, and the solve was removed in vacuo. The product was used as is for the next reaction.

In a like manner, the following additional compound were prepared:

(b) 5-Bromo-3-(2-pyrrolidinylethyl)-1 H-indole: (72%) from 5-bromo-3-(1-pyrrolidinylglyoxyl)-1 H-indole (Example 2a). (c) (S)-5-Bromo-3-[(N-methylpyrrolidin-2-yl)methyl]- H-indole: (57%) from (S)-3-(N-benzyloxycarbonylpyrrolidin-2-ylcarbonyl)-5-bromo-1 H-indole (Example 1b).

(d) (R)-5-Bromo-3-[(N-methylpyrrolidin-2-yl)methyl] 1 H-indole: (63%) from (R)-3-(N-benzyloxycarbonylpyrrolidin-2-ylcarbonyl)-5-bromo-1H-indole (Example 1a).

Example 4(a): (S)-5-Bromo-1-(t-butyldimethylsilyl)-3-[(N-methylpyrrolidin-2-yl)methyl]indole To a solution of (S)-5-bromo-3-[(N-methylpyrrolidin-2-yl)methyl]-1 H-indole (Example 3c, 1.00 g, 3.41 mmol) in THF (15 mL) under argon, was added sodium hexamethyldisilazide (6.82 mL, 6.82 mmol and the resulting solution was stirred at room temperature for 20 min. The reaction mixture was cooled to 0° C. and to this was added a solution of t-butydimethylsilyl chloride (1.03 g, 6.82 mmol) in THF (4 mL) and the resulting culture was warmed to room temperature and stirred for 1 hour. The solvent as removed in vacuo and the resulting product was diluted with water (10 mL) and extracted with ethyl acetate (2×10 mL). The ethyl acetate extract was washed with brine (10 mL), dried (Na$_2$SO$_4$), filtered and the filtrate was evaporated to dryness. The crude residue was subjected to flash silica gel chromography to afford the title compound as a yellow oil (1.07 g, 79%). $^{13}$C NMR (CDCl$_3$)δ: 140.1, 133.1, 129.8, 124.1, 121.5, 115.8, 115.2, 112.7, 66.2, 7.6, 40.9, 31.6, 30.1, 26.2, 21.9, 19.5, –3.96

In a like manner, the following additional compounds were prepared:

(b) (R)-5-Bromo-1-(t-butyldimethylsilyl)-3-[(N-methylpyrrolidin-2-yl)methyl]indole: (1.05 g, 77%) as a yellow oil from (R)-5-bromo-3-[(N-methylpyrrolidin-2-yl)methyl]-1H-indole (Example 3d, 1.00 g, 3.41 mmol), sodium hexamethyldisilazide (6.82 mL, 6.82 mmol) and t-butyldimethylsilyl chloride (1.03 g, 6.82 mmol). $^{13}$C NMR (CDCl$_3$)6: 140.1, 133.1, 129.8, 124.1, 121.5, 115.8, 115.2, 112.7, 66.2, 57.6, 40.9, 31. , 30.1, 26.3, 21.9, 19.5, −3.95.

(c) 5-Bromo-1-(t-butyldimethylsilyl)-3-[2-(N N-dimethylamino)ethyl]indole: (0.61 g, 85%) as a brown oil from 5-bromo-3-[2-(N,N-dimethylamino)ethyl]-1 H-indole (Example 3a, 0.50 g, 1.87 mmol), sodium hexamethyidisilazide (3.74 mL, 3.74 mmol) and t-butyldimethylsilyl chloride (0.56 g, 3.74 mmol). $^{13}$C. NMR (CDCl$_3$): 140.1, 132.8, 129.5, 124.2, 121.3, 115.8, 115.3, 112.7, 60.1, 45.4, 26.3, 23.6, 19.5, −3.99.

(d) 5-Bromo-1-(t-butyldimethylsilyl)-3-(2-pyrrolidin lethyl)indole: (1.02 g, 73%) as a brown oil from 5-bromo-3-(2-pyrrolidinylethyl)-1H-indole (Example 3b, 1.00 g, 3.4 mmol), sodium hexamethyldisilazide (82 mL, 6.82 mmol) and t-butyldimethylsilyl chloride (6.82 mL. 6.82 mmol). $^{13}$C NMR (CDCl$_3$): 140.1, 132.9, 129.4, 124.1, 121.5, 116.3, 115.2, 112.7, 6.9, 54.3, 26.3, 25.1, 23.5, 19.5, −3.98.

Example 5(a): 1-(t-Butyldimethylsilyl)-5-[(7-R,S)(8a-R,S)-7-hydroxyoctahydroindolizin-7-yI]-3-{[(2S)-N-methyl)yrrolidin-2-yl]methyl}indole In a 25 mL flame dried, round bottom flask equipped with a stir bar under argon was added (S)-5-bromo-1-(t-butyldimethylsilyl)-3-[(N-methylpyrrolidin-2-yl)methyl]indole (Example 4a, 0.50 g, 1.26 mmol ) and THF (6 mL). The mixture was cooled to −78 ° C., and butyllithium (1.7 M in hexane; 1.26 mmol) was added dropwise. The resulting mixture was stirred at −78° C. for 50 min., followed by the addition of a solution of octahydroindolizin-7-one (King, F. D., J. Chem. Soc. Perkin Trans. I, 1986:447–453, 0.4 g, 3.15 mmol) in THF (4 mL). The resulting mixture was warmed up to −5 and stirred for a further 1 hour. The reaction mixture was then poured into a pH 7 buffer (5 mL) at 0° C., extracted into ethyl acetate (2×10 mL) and the combined organic phases were washed successively with water (10 mL) and brine (10 mL). The organic layer was dried (Na$_2$SO$_4$), filtered and the filtrate was evaporated to dryness in vacuo. The crude residue was subjected to flash silica gel chromatography to afford the title compound as a yellowish white foamy solid (0.25 g, 43%). $^{13}$C NMR (CDCl$_3$)5: 140.6, 135.2, 130.8, 128.9, 120.4, 116.8, 116.4, 114.1, 73.4, 66.5, 61.5, 57.6, 53.2, 49.8, 44.8, 40.9, 38.3, 31.6, 30.2, 30.0, 26.3, 21.9, 21.8, 19.5, −3.96.

In a like manner, the following additional compounds were prepared:

(b) 1-(t-Butyldimethylsilyl)-5-[(7-R,S)(8a-R,S)-7-hydroxyoctahydroindolizin-7-yl]-3-{[(2R)-N-methylpyrrolidin-2-yl]methyl}indole: (0.19 g, 33%) as a white foamy solid from (R)-5-bromo-1-(t-butyldimethylsilyl)-3-[(N-methylpyrrolidin-2-yl)methyl]indole (Example 4b, 0.50 g, 1.26mmol) and octahydroindolizin-7-one (0.44 g, 3.15 mmol). $^{13}$C NMR (CDCl$_3$)5: 140.6, 135.2, 130.8, 128.9, 120.4, 116.7, 116.3, 114.1, 73.3, 66.6, 61.5, 57.5, 53.2, 0.4, 49.7, 43.9, 40.8, 38.2, 31.6, 30.2, 29.9, 26.3, 21.8, 21.7, 19.4, −3.97.

(c) 1-(t-Butyldimethylsilyl)-5-[(7-R or S)(8a-R,S)--hydroxyoctahydroindolizin-7-yl]-3-[2-(N,N-dimethylamino)ethyl]indole: (0.11g, 22%) isomer 1, isolated as a white foamy solid from 5-bromo-1-(t butyldimethylsilyl)-3-[2-(N,N-dimethylamino)ethyl]indole (Example 4c). $^{13}$C NMR(CDCl$_3$): 140.6, 140.1, 130.7, 128.6, 118.5, 116.5, 114.1, 113.7, 72.9, 30.3, 59.7, 53.8, 48.6, 45.5, 44.6, 39.2, 30.3, 26.3, 23.8, 21.3, 19.5, −3.96.

(d) 1-(t-Butyldimethylsilyl)-5-[(7-R or S)(8a-R,S)-7-hydroxyoctahydroindolizin-7-yl]-3-[2-(N,N-dimethylamino)ethyllindole: (0.14 , 27%) isomer 11, isolated as a white foamy solid from 5-bromo-1-(t-butyldimethylsilyl)-3-[2-(N,N-dimethylamino)ethyl]indole (Example 4c). $^{13}$C NMR (CDCl$_3$): 140.7, 135.3, 130.7, 128.6, 120.4, 116.6, 114.1, 73.5, 61.5, 6.4, 53.2, 49.8, 45.6, 44.1, 38.2, 30.3, 26.3, 23.8, 21.8, 19.5, −3.98.

(e) 1-(t-Butyldimethylsilyl)-5-[(7-R,S)(8a-R,S)-7-hydroxyoctahydroindolizin-7-yl]-3-(2-pyrrolidinylethyl)indole: (0.12 g, 38%) as pale, yellow, fluffy solid from 5-bromo-I-(t-butyldimethylsilyl)-3-(2-pyrrolidinylethyl)indole (Example 4d, 0.27 g, 0.65 mmol) as a mixture of 2 isomers. Isomer I: $^{13}$C NMR (CDCl$_3$) : 140.7, 135.3, 130.6, 128.7, 120.3, 116.6, 116.4, 14.1, 73.3, 61.4, 57.0, 54.2, 53.1, 49.5, 43.6, 37.9, 30.0, 26.3, 24.8, 23.5, 21.7, 19.4, −4.0. Isomer 2: $^{13}$C NMR (CDCl$_3$) : 140.4, 140.0, 130.7, 128.6, 118.6, 116.7, 114.2, 113.7, 72.9, 59.7, 57.1, 54.2, 53.7, 48.6, 44.5, 39.1, 30.3, 26 3, 25.1, 23.5, 21.2, 19.4, −4.0.

Example 6(a): 5-[(7-R,S)(8a-R,S)-7-Hydroxyoctahydroindolizin-7-yI]-3-{[(2S)-N-methylpyrrolidin-2-yl]methyl}-1 H-indole To a solution of 1-(t-butyldimethylsilyl)-5-[(7-R,S)(8a-R,S)-7-hydroxyoctahydroindolizin-7-yl]-3-{[(2S)-N-methyl yrrolidin-2-yl]methyl}indole (Example 5a, 0.07 g, 0.15 mmol) in THF (1 mL), was added tetrabutylammonium fluoride (0.21 mL, 0.32 mmol), dropwise. The reaction mixture was stirred at room temperature for min. The reaction was quenched with water (2 mL) and extracted with ethyl acetate (2×10 mL). The ethyl acetate extract was washed with brine (10 mL), dried (Na$_2$SO$_4$), filtered and the filtrate was evaporated to dryness in vacuo. The resulting residue was subjected to flash silica gel chromatograph to afford the title compound as a white foamy solid (0.04 g, 72%). HRM (FAB) MH$^+$ calculated for C$_{22}$H$_{32}$N$_3$O: 354.25455, found 354.25641.

In a like manner, the following addition compounds were prepared:

(b) 5-[(7-R,S)(8a-R,S)-7-Hydroxyoctahydroindolizin-7-yl]-3-{[(2R)-N-methylpyrrolidin-2-yl]methyl}-1H-indole: (0.03 g, 5%) as an off-white solid from I-(t-butyldimethylsilyl)-5-[(7-R,S)(8a-R,S)-7-hdroxyoctahydroindolizin-7-yl]-3-{[(2R)-N-methylpyrrolidin-2-yl]methyl}indole (Example 5b, 0.07 g, 0.15mmol). HRMS (FAB): MH$^+$ calculated for C$_{22}$H$_{32}$N$_3$O: 354.25455, found 354.25257.

(c) 5-[(7-R or S)(8a-R,S)-7-Hydroxyoctahydroindolizin-7-yl]-3-[2-(N,N-dimethylamino)ethyl]indole: (0.007g, 43%) as yellow paste from 1-(t-butydimethylsilyl)-5-[(7-R or S)(8a-R,S)-7-hydro octahydroindolizin-7-yl]-3-[2-(N,N-dimethylamino)ethyl]indole, Isomer I (Example 5c, 0.02g, 0.05mmol).

(d) 5-[(7-R or S)(8a-R,S)-7-Hydroxyoctahydroindolizin-7-yl]-3-[2-(N,N-dimethylamino)ethyl]indole: (0.009g, 55%) as yellow paste from 1-(1-butyldimethylsilyl)-5-[(7-R or S)(8a-R,S)-7-hydro octahydroindolizin-7-yl]-3-[2-(N,N-dimethylamino)ethyl]indole, Isomer II (Example 5d, 0.02g, 0.05mmol).

Example 7(a): 5-[(8a-R,S)-1,2,3,5,6,8a-Hexahydroindolizin-7-yl]-3-{[(2S)-N-methylpyrrolidin-2-yl]methyl}-1 H-indole A solution of the 5-[(7-R,S)(8a-R,S)-7-hydroxyoctahydroindolizin-7-yl]-3-{[(2S)-N-methylpyrrolidin-2-yl]methyl}-1H-indole (Example 6a, 0.13 g, 0.2 mmol) and trifluoroacetic acid (40% by volume) in methylene chloride (2.52 mL) under argon was heated at reflux for 20 hour. The solvent was removed in vacuo and 1

N sodium hydroxide (15 mL) was added to adjust the solution to a pH of ~8–9. The resulting solution was extracted with ethyl acetate (10 mL). The ethyl acetate extract was washed with water (2×10 mL), brine (10 mL), dried (sodium sulfate), filtered and the filtrate was evaporated to dryness in vacuo. The crude reaction mixture was subjected to flash silica gel chromatography to afford two isomers. The major isomer was the title compound and was isolated as a lemon yellow foamy solid (0.05 g, 48%). $^{13}C$ NMR (CDCl$_3$)δ: 135.8, 135.7, 132.5, 127.8, 124.2, 22.7, 119.5, 115.2, 113.9, 110.9, 66.7, 60.2, 57.5, 51.5, 46.9, 40.8, 31.6, 30.3, 29.9, 25.9, 22.7, 21.9.

In a like manner, the following additional compounds were prepared:

(b) 5-[(8a-R,S)-1,2,3,5,8,8a-Hexahydroindolizin-7-yl]-3-{[(2S)-N-methylpyrrolidin-2-yl]methyl}-1 H-indole: (0.03 g, 2%) light yellow foamy solid isolated as the minor isomer in the above dehydration of 5-[(7-R,S)(8a-R,S)-7-hydroxy-1,2,3,5,6,8a-hexahydroindolizin-7-yl]-3-{[( S)-N-methylpyrrolidin-2-yl]methyl}-1H-indole (Example 6a).

(c) 5-[(8a-R,S)-1,2,3,5,6,8a-Hexahydroindolizin-7-yl]-3-{[(2R)-N-methylpyrrolidin-2-yl]methyl}-1 H-indole: (0.03 g, 47%, major isomer) as a bright yellow oil from the dehydration of 5-[(7-R,S)(8a-R,S)-7-hydroxyoctahydroindolizin-7-yl]-3-{[(2R)-N-methyl yrrolidin-2-yl]methyl}-1 H-indole (Example 6b, 0.10 g, 0.22 mmol). $^{13}C$ NMR (CDCl$_3$)6: 135.8, 135.6, 132.5, 127.7, 124.1, 122.6, 119.6, 115.1, 114.0, 10.9, 66.7, 60.1, 57.5, 51.4, 46.8, 40.8, 31.5, 30.2, 29.8, 25.8, 22.7, 21.8; HRMS (FAB): MH$^+$ calculated for $C_{22}H_{30}N_3$: 336.24399, found 336.24481.

(d) 5-[(8a-R,S)-1,2,3,5,8,8a-Hexahydroindolizin-7-yl]-3-{[(2R)-N-methylpyrrolidin-2-yl]methyl}-1H-indole: (0.02 g, 31%, minor isomer) as a bright yellow oil from the dehydration of 5-[(7-R,S)(8a-R,S)-7-hydroxyoctahydroindolizin-7-yl]-3-{[(2R)-N-methyl pyrrolidin-2-yl]methyl}-1 H-indole (Example 6b, 0.10 g, 0.22 mmol). $^{13}C$ NMR (CDCl$_3$)6: 136.9, 135.6, 132.9, 127.7, 122.4, 120.5, 119.9, 115.4, 115.3, 114.2, 110.8, 66.7, 60.5, 57.5, 54.3, 53.0, 40.8, 35.4, 31.5, 30.9, 29, 2.8, 21.5; HRMS (FAB): MH$^+$ calculated for $C_{22}H_{30}N_3$: 336.24399, found 336.24 62.

(e) 5-[(8a-R,S)-1,2,3,5,8,8a-Hexahydroindolizin-7-yl]-3-[2-(N$_7$N-dimethylamino)ethyl]indole: (0.05 g, 41%, major isomer) as a yellow solid from from 5-[(7-R,S)(8a-R,S)-7-hydroxyoctahydroindolizin-7-yl]-3-[2-(N,N-dimethylamino)ethyl]indole (Examples 6c and 6d 0.19 g, 0.42 mmol). $^{13}C$ NMR(CDCl$_3$): 136.8, 135.8, 132.7, 127.4, 122.3, 20.3, 119.8, 115.1, 114.0, 111.0, 60.5, 60.3, 54.2, 52.9, 45.4, 35.3, 30.9, 23.7 21.5.

(f) 5-[(8a-R,S)-1,2,3,5,6,8a-Hexahydroindolizin-7-yl]-3-[2-(N,N-dimethylamino)ethyl]indole: (0.04 g, 30%, minor isomer) as a yellow paste from from 5-[(7-R,S)(8a-R,S)-7-hydroxyoctahydroindolizin-7-yl]-3-[2-(N,N-dimethylamino)ethyl]indole (Examples 6c and 6d 0.19 g, 0.42 mmol). t$^3$C NMR (CDCl$_3$): 135.9, 135.7, 132.4, 127.5, 123.8, 122.3, 119.6, 114.9, 114.2, 111.1, 60.3, 60.1, 51.4, 46.7, 45.4, 30.3, 25.7, 23.7, 22.7.

(g) 5-[(8a-R,S)-1,2,3,5,6,8a-Hexahydroindolizin-7-yl]-3-(2-pyrrolidinylethyl)indole: (24 mg, 29%, major isomer) as a yellow sticky solid from 1-(t-butyldimethylsilyl)-5-[(7-R,S)(8a-R,S)-7-h droxyoctahydroindolizin-7-yl]-3-(2-pyrrolidinylethyl)indole (Example 5e, 0.1 g, 0.25 mmol). $^{13}C$ NMR (CDCl$_3$) : 136.0, 135.9, 131.6, 127.2, 122.8, 10.8, 119.6, 115.2, 113.0, 111.3, 59.7, 56.6, 54.0, 51.3, 46.0, 30.3, 29.7, 23.8, 23.4, 22.5.

(h) 5-[(8a-R,S)-1,2,3 5,8,8 a-Hexahydroindolizin-7-yI]-3-(2-pyrrolidinylethyl)indole: (20 mg, 24%, minor isomer) as a pale yellow sticky solid from I -(t-butyldimethylsilyl)-5-[(7-R,S)(8a-R,S)-7-hydroxyoctahydroindolizin-7-yl]-3-(2-pyrrolidinylethyl)indole (Example 5e, 0.12 g, 0.25 mmol). $^{13}C$ NMR (CDCl$_3$): 136.7, 135.7, 133.0, 127.4, 122.0, 120.4, 120.0, 115.3, 114.6, 110.9, 60.5, 57.2, 54.3, 5.2, 53.0, 35.4, 30.9, 25.0, 23.5, 21.6.

Example 8(a): 5-[(7R or 7S)(8a-R,S)-Octahydroindolizin-7-yl]-3-{[(2S)-N-methylpyrrolidin-2-yl]methyl}-1 H-indole (major isomer) and (b) 5-[(7R or 7S)(8a-R,S)-Octahydroindolizin-7-yl] 3-{[(2S)-N-methylpyrrolidin-2-yl]methyl}-1 H-indole (minor isomer)

To a 25 mL round bottom flask, was added 10% Pd/C (1 scoop) under argon. To this was added ethanol (3 mL), followed by a mixture of 5-[(7-R,S)(8a-R,S)-1,2,3,5,6,8a-hexahydroindolizin-7-yl]-3-{[(2S) -N-methylpyrrolidin-2-yl]methyl}-1 H-indole and 5-[(7-R,S)(8a-R,S)-1,2,3,5,8,8a-hexahydroindolizin-7-yl]-3-{[(2S)-N-methylpyrrolidin-2-yl]methyl}-1H-indole (Examples 7a and 7b, 0.06 g, 0.17mmol) in ethanol (4 mL). The argon line was removed and a hydrogen balloon was attached through a two way tap. The flask was evacuated using a water aspirator, then filled with hydrogen gas. The reaction mixture was stirred at room temperature under hydrogen overnight, then filtered through a pad of celite, evaporated to dryness and subjected to flash silica gel chromatography to afford a major isomer (0.03 g, 53%) as a white solid and a minor isomer (0.007 g, 12%) as a brown oil. $^{13}C$ NMR (major isomer, CDCl$_3$)6: 137.3, 135.1, 127.8, 122.3, 121.5, 116.4, 110.9, 66.6, 64.8, 57.5, 54.0, 52.8, 43.4, 40.8. 39.4, 39.3, 34.3, 3 4.2, 31.6, 30.5, 29.9, 21.8, 21.2.

In a like manner the following additional compound was prepared:

(c) 5-[(7-R,S)(8a-R,S)-Octahydroindolizin-7-yl]- -{[(2R)-N-methylpyrrolidin-2-yl]methyl}-1H-indole: (0.005 g. 15%) as a clear oil from 5-[(7-R,S)(8a-R,S)-1,2,3,5,6,8a-hexahydroindolizin-7-yl]-3-{[(2R)-N ethylpyrrolidin-2-yl]methyl}-1H-indole (Example 6c, 0.03 g, 0.10 mmol). HRMS (FAB): MH$^+$ calculated for $C_{22}H_{32}N_3$: 338.25961, found 338.26022.

TABLE 1

Summary of Exemplified Compounds of Formula I

| Example # | Structure |
|---|---|
| 6b | 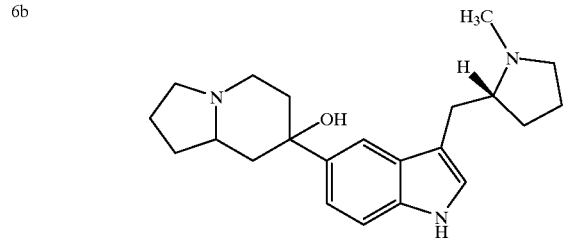 |
| 6c | 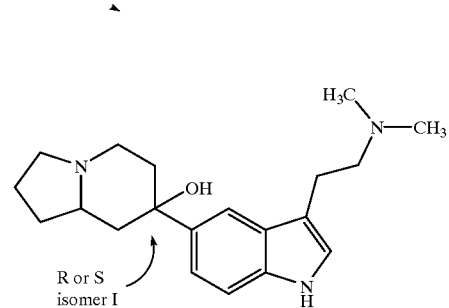 |

TABLE 1-continued

Summary of Exemplified Compounds of Formula I

| Example # | Structure |
|---|---|
| 6d | (R or S isomer II) |
| 7c | 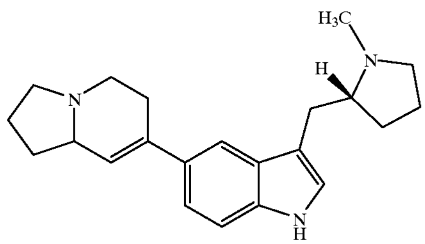 |
| 7d | 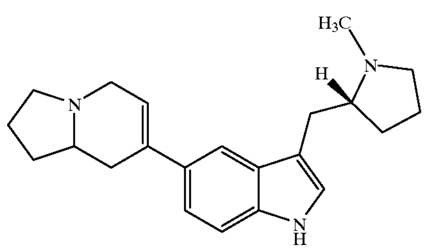 |
| 7e | 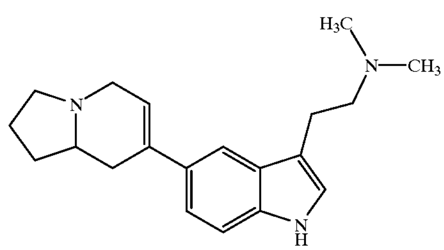 |
| 7f | 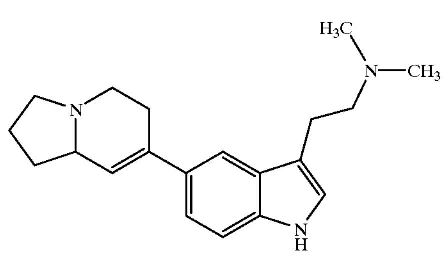 |
| 7g | |
| 7h | |
| 8c | |

Example 9: General Procedure for salt formation:
Hydrochloric acid: acid (4 mol. equiv., 1M in diethyl ether) is added to a solution of the substrate (1 mol. equiv.) in dichloromethane (approx. 0.1 M solution) and the mixture is stirred for 20 min. The and excess acid are removed in vacuo and the crude product is recrystallized from methanol ether. Other salts: The appropriate acid (2 mol. equiv. solid acids) are added to a solution of the substrate (1 mol. equiv.) in methanol (0.14 M solution) and the mixture is stirred overnight. The solvent is removed in vacuo and the crude product is purified.

Example 10: Comparison of the Binding Affinities

Selected compounds of the previous examples, as well as reference compounds were evaluated for binding affinity using cell types receptive specifically to $5\text{-HT}_{1D}$ and $5\text{-HT}_{1B}$ ligands. The assay protocol generally entailed the incubation of membranes prepared f cells expressing the $5\text{-HT}_{1D}$ or $5\text{-HT}_{1B}$ subtype of 5-HT receptors with $^3$H serotonin (1 nM for $5\text{-HT}_1$D and 2.5 nM for $5\text{-HT}_{1B}$). Specific concentrations of the test compound were incubated with the radioligand and the membrane homogenates prepared from the recombinant cells. After a 60 minute incubation at 22° C., the incubation was terminated by vacuum filtration. The filters were washed with buffer and counted for radioactivity using liquid scintillation spectroscopy. The affinity of the test compound for the $5\text{-HT}_{1D}$ receptor is expressed as the amount (in percent) of binding of the radioligand that is inhibited in the presence of 100 nM of test compound. A greater percent inhibition indicates greater affinity for the $5\text{-HT}_{1D}$ receptor. Selected compounds of the invention showed an affinity of greater than 50% for the 5-HT$_{1D}$ receptor. Specific compounds of the invention, for example, those of examples 6b, 7c, 7d and 8c showed an affinity of greater than 75% for the 5-HT$_{1B}$ receptor. More specific compounds of the invention, for example, those of examples 6c and 7d showed an affinity of greater than 90% for the 5-HT$_{1D}$ receptor. In terms of selectivity, selected compounds of the invention had an affinity less than 50% for the 5-HT$_{1B}$ receptor. Specific compounds, for example those of examples 6b and 8c showed an affinity of less 30% for the 5-HT$_{1B}$ receptor. Compounds of the previous examples where the stereochemistry at the 2-position of the pyrrolidine ring is S (that is those of Examples 6a, 7a, 7b, 8a and 8b), showed little, if any, binding at both the 5-HT$_{1D}$ and 5-HT$_{1B}$ receptors at a concentration of 100 nM.

Example 11: Pharmaceutical Examples

Tablets

These may be prepared by the normal methods such as wet granulation or direct compression.

A. Direct Compression

|  | mg/tablet |
| --- | --- |
| Active ingredient | 10.0 |
| Microcrystalline Cellulose USP | 188.5 |
| Magnesium Stearate BP | 1.5 |
| Compression weight | 200.0 |

The active ingredient is sieved through a suitable sieve, blended with the excipients and compressed using 7 mm diameter punches. Tablets of other strengths may be prepared by altering the compression weight and using punches to suit.

B. Wet Granulation

|  | mg/tablet |
| --- | --- |
| Active ingredient | 10.0 |
| Lactose BP | 143.5 |
| Starch BP | 30.0 |
| Pregelatinised Maize Starch BP | 15.0 |
| Magnesium Stearate BP | 1.5 |
| Compression weight | 200.0 |

The active ingredient is sieved through a suitable sieve and blended with lactose, starch and pregelatinised maize starch. Suitable volumes of purified water are added and the powders are granulate. After drying, the granules are screened and blended with the magnesium stearate. The granules are then compressed into tablets using 7 mm diameter punches.

C. For Buccal Administration

|  | mg/tablet |
| --- | --- |
| Active ingredient | 10.0 |
| Lactose BP | 86.8 |
| Sucrose BP | 86.7 |
| Hydroxypropyl methylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellullose. Suitable volumes of purified water are added and the powders are granulated. After drying, the granules are screened and blended with the magnesium stearate. The granules are then compressed into tablets using suitable punches.

The tablets may be film-coated with suitable film forming materials, such as hydroxypropyl methylcellulose, using standard techniques. Alternatively the tablets may be sugar coated.

Capsules

|  | mg/capsule |
| --- | --- |
| Active ingredient | 10.0 |
| *Starch 1500 | 89.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weigh and if necessary changing the capsule size to suit.

Syrup

|  | mg/5 ml dose |
| --- | --- |
| Active ingredient | 10.0 |
| Sucrose BP | 2750.0 |
| Glycerine BP | 500.0 |
| Buffer | as required |
| Flavour | as required |
| Colour | as required |
| Preservative | as required |
| Distilled water to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The soup produced is clarified by filtration.

Suppositories

| Active ingredient | 10.0 mg |
| --- | --- |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

Injection for Intravenous Administration

|  | % w/v |
| --- | --- |
| Active ingredient | 0.2 |
| Sodium Chloride BP | as required |
| Water for Injection BP to | 100.00 |

Sodium chloride may be added to adjust the molton city of the solution and the pH may be adjusted, using acid or alkali, to that of optimum stability and/or to facilitate solution of the active ingredient. Alteratively suitable buffer salts may be used.

The solution is prepared, clarified and filled into appropriate size ampoules sealed by fusion of the glass. The injection is sterilized by heating in an autoclave using one of the acceptable cycles. Alternatively the solution may be sterilized by filtration and filled into sterile ampoules under aseptic conditions. The solution may be packed under an inert atmosphere of nitrogen or other suitable gas.

Inhalation Cartridges

| | mg/cartridge |
|---|---|
| Active ingredient micronised | 1.0 |
| Lactose BP | 39.0 |

The active ingredient is micronised (Microniser is Registered Trade Mark) in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler (Registered Trade Mark).

Metered Dose Pressurized Aerosol

| | mg/metered dose | per can | |
|---|---|---|---|
| Active ingredient micronised | 0.500 | 120.0 | mg |
| Oleic Acid BP | 0.050 | 12.0 | mg |
| Trichlorofluoromethane BP | 22.250 | 5.34 | mg |
| Dichlorofluoromethane BP | 62.2 | 14.92 | g |

The active ingredient is micronised in a fluid energy mill to a fine particle size range. The oleic acid is mixed with the trichlorofluoromethane at a temperature of 10–15° C. and the pulverized drug is mixed into the solution with a high shear mixer. The suspension is metered into aluminum aerosol cans and suitable metering valves, delivering a metered amount of 85 mg of suspension, are crimped onto the cans and the dichlorodifluoromethane is pressure filled into the cans through the valves.

We claim:

1. A compound according to Formula I and a salt, solvate or hydrate thereof,

I wherein:

$R^1$ is selected from the group consisting of $CR^5R^6CH_2NR^7R^8$ group of Formula II:

II $R^2$ is selected from the group consisting of H, OH, $C_{1-6}$alkyl and $C_{1-6}$ alkoxy;

$R^3$ is selected from the group consisting of H, OH, $C_{1-6}$alkyl, $C_{1-6}$alkoxy, $C_{1-6}$alkylthio and optionally substituted benzyloxy;

n is selected from the group consisting of a integer of from 1–3;

Z is selected from the group consisting of C and N;

——— represents a single or double bond provided that only one double bond is present in the ring at a time;

$R^4$ is selected from the group consisting of H, OH, $C_{1-6}$alkoxy or null, provided that when $R^4$ is selected from the group consisting of H, OH and $C_{1-6}$alkoxy, Z is C and ——— represents a single bond and when $R^4$ is null, either Z is C and ——— represents a double bond or Z is N and ——— represents a single bond;

one of $R^5$ and $R^6$ is independently selected from H, $C_{1-6}$alkyl, $C_{1-6}$alkoxy and hydroxy and the other of $R^5$ and $R^6$ is F;

$R^7$ and $R^8$ are independently selected from H and $C_{1-6}$-alkyl or $R^7$ and $R^8$ form an alkylene bridge which optionally incorporates a heteroatom selected from O, $NR^9$ and S, and which, together with the nitrogen atom to which they are attached, creates ail optionally substituted 3- to 7-membered carbo- or heterocyclic ring; and $R^9$ is selected from the group consisting H, $C_{1-6}$-alkyl and optionally substituted benzyl.

2. A compound according to claim 1, wherein $R^1$ is $CR^5R^6CH_2NR^7R^8$.

3. A compound according to claim 2, wherein $R^5$ and $R^6$ are both H and $R^7$ and $R^8$ are independently selected from H and methyl or $R^7$ and $R^8$ form an alkylene bridge which, together with the nitrogen atom to which they are attached, creates an unsubstituted 5- to 6-membered ring.

4. A compound according to claim 3, wherein $R^5$ and $R^6$ are both H and either $R^7$ and $R^8$ are both methyl or $R^7$ and $R^8$ form an alkylene bridge which, together with the nitrogen atom to which they are attached, creates an unsubstituted pyrrolidine ring.

5. A compound according to claim 1, wherein $R^9$ is a group of Formula II.

6. A compound according to claim 5, wherein $R^9$ is selected from the group consisting of H, methyl, ethyl and benzyl, wherein benzyl is optionally substituted with 1 group independently selected from halo, OH, methyl, methoxy, methylthio, $CF_3$ and $CF_3O$.

7. A compound according to claim 6, wherein $R^9$ is methyl.

8. A compound according to claim 1, wherein $R^2$ is H.

9. A compound according to claim 1, wherein $R^3$ is H.

10. A compound according to claim 1, wherein $R^2$ and $R^3$ are both H.

11. A compound according to claim 1, wherein n is selected from the group consisting of an integer of from 1–2.

12. A compound according to claim 11, wherein n is 1.

13. A compound according to claim 1, wherein is C.

14. A compound according to claim 13, wherein and ——————— are selected to form a bicycle selected from octahydroindolizin-7-yl, 1,2,3,5,6,8a-hexahydroindolizin-7-yl and 1,2,3,5,8,8a-hexahydroindolizin-7-yl.

15. A compound according to claim 1, which is selected from the group consisting of:

5-[(7-R,S)(8a-R,S)-7-Hydroxyoctahydroindolizin-7-yl]-3-{[(2R)-N-methylpyrrolidin-2-yl]methyl}-1 H-indole;

5-[(7-R,S)(8a-R,S)-1,2,3,5,6,8a-Hexahydroindolizin-7-yl]-3-{[(2R)-N-methylpyrrolidin-2-yl]methyl}-1 H-indole;

5-[(7-R,S)(8a-R,S)-1,2,3,5,8,8a-Hexahydroindolizin-7-yl]-3-{[(2R)-N-methylpyrrolidin-2-yl]methyl}-1 H-indole;

5-[(7-R,S)(8a-R,S)-Octahydroindolizin-7-yl] 3-{[(2R)-N-methylpyrrolidin-2-yl]methyl}-1 H-indole;

5-[(7-R,S)(8a-R)-7-Hydroxyoctahydroindolizin-7-yl]-3-[2-(N,N-dimethylamino)ethyl]indole;

5-[(7-R,S)(8a-S)-7-Hydroxyoctahydroindolizin-7-yl]-3-[2-(N,N-dimethylamino)ethyl]indole;

5-[(8a-R,S)-1,2,3,5,8,8a-Hexahydroindolizir-7-yl]-3-[2-(N,N-dimethylamino)ethyl]indole;

5-[(8a-R,S)-1,2,3,5,6,8a-Hexahydroindoliziri-7-yl]-3-[2-(N,N-dimethylamino)ethyl]indole;

5-[(8a-R,S)-1,2,3,5,6,8a-Hexahydroindoliziri-7-yl]-3-(2-pyrrolidinylethyl)indole; and 5-[(8a-R,S)-1,2,3,5,8,8a-Hexahydroindolizir I-7-yl]-3-(2-pyrrolidinylethyl)indole.

16. A compound according to claim 1, which is selected from the group consisting of:

5-[(7-R,S)(8a-R,S)-7-Hydroxyoctahydroindolizin-7-yl]-3-{[(2R)-N-methylpyrrolidin-2-yl]methyl}-1 H-indole;

5-[(7-R,S)(8a-R,S)-1,2,3,5,6,8a-Hexahydroindolizin-7-yl]-3-{[(2R)-N-methylpyrrolidin-2-yl]methyl}-1 H-indole;

5-[(7-R,S)(8a-R,S)-1,2,3,5,8,8a-Hexahydroindolizin-7-yl]-3-{[(2R)-N-methylpyrrolidin-2-yl]methyl}-1 H-indole; and 5-[(7-R,S)(8a-R,S)-Octahydroindolizin-7-yl] 3-{[(2R)-N-methylpyrrolidin-2-yl]methyl}-1 H-indole.

17. A pharmaceutical composition, comprising a pharmaceutically acceptable carrier and a compound according to claim 1 in an amount effective to stimulate a 5-$HT_{1D}$ receptor.

18. A pharmaceutical composition, comprising a pharmaceutically acceptable carrier and a compound according to claim 15 in an amount effective to stimulate a 5-$HT_{1D}$ receptor.

19. A method for treating a patient having a medical condition for which stimulation of the 5-$HT_{1D}$ receptor is indicated, comprising the step of administering to the patient a pharmaceutical composition as defined in claim 17.

20. A method for treating a patient according to claim 19, wherein the medical condition is migraine.

21. The compound according to claim 1, wherein said compound has the following formula:

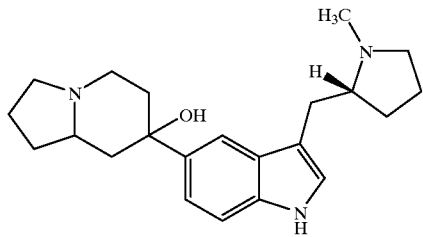

* * * * *

UNITED STATES PATENT AND TRADEMARK OFFICE
CERTIFICATE OF CORRECTION

PATENT NO. : 6,329,390 B1  
DATED : December 11, 2001  
INVENTOR(S) : Slassi et al.

Page 1 of 1

It is certified that error appears in the above-identified patent and that said Letters Patent is hereby corrected as shown below:

Column 2,
Lines 16, 21, 22 and 23, please change the solid line "____" to dashes -- ---- --.

Column 4,
Lines 62 and 65, please change the solid line "____" to dashes -- ---- --.

Column 5,
Lines 19, 39 and 41, please change "hexahydroindolizir" to -- hexahydroindolizin --.
Line 49, please change "hexahydroindolizii" to -- hexahydroindolizin --.

Column 6,
Line 15, please change the solid line "____" to dashes -- ---- --.

Column 7,
Line 24, please change the solid line "____" to dashes -- ---- --.

Column 8,
Lines 52, 54 and 55, please change the solid line "____" to dashes -- ---- --.

Column 26,
Lines 18, 24, 25 and 26, please change the solid line "____" to dashes -- ---- --.

Column 27,
Line 2, after "wherein" please insert the variable -- Z --.
Lines 24, 26, 28 and 29, please change "hexahydroindolizir" to -- hexahydroindolizin --.

Signed and Sealed this

Third Day of September, 2002

Attest:

JAMES E. ROGAN  
*Attesting Officer*          *Director of the United States Patent and Trademark Office*